Feb. 20, 1945. E. A. BRIGGS Plant Pat. 650
GLADIOLUS PLANT
Filed Aug. 30, 1944
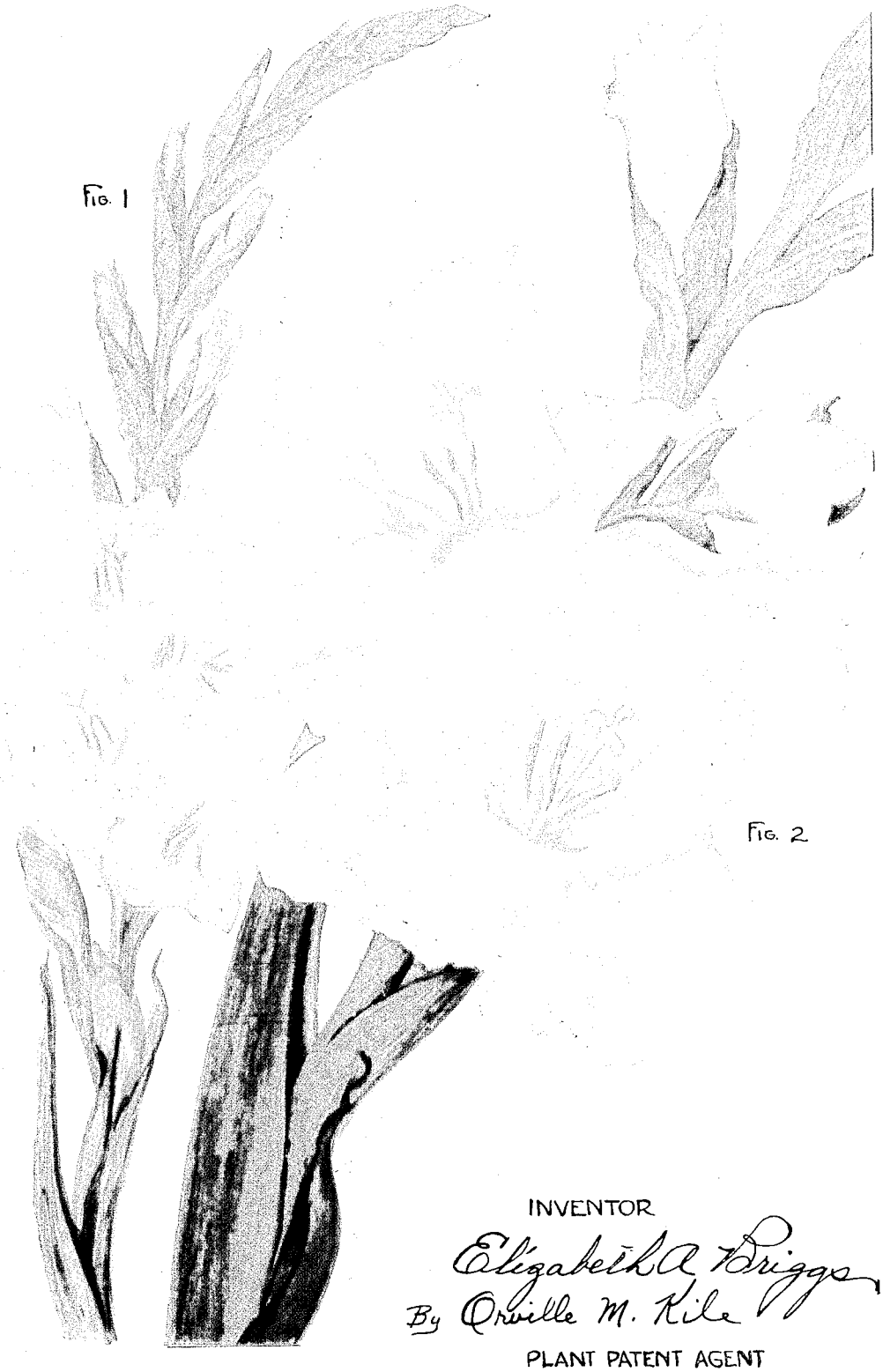
INVENTOR
Elizabeth A. Briggs
By Orville M. Kile
PLANT PATENT AGENT Patented Feb. 20, 1945

Plant Pat. 650

UNITED STATES PATENT OFFICE

650

GLADIOLUS PLANT

Elizabeth A. Briggs, Encinitas, Calif., assignor to
Donald A. Briggs, Encinitas, Calif.

Application August 30, 1944, Serial No. 551,856

1 Claim. (Cl. 47—60)

My present invention relates to a new and improved variety of gladiolus and is notable particularly for size and quantity of bloom of excellent substance and shipping quality and of a distinctive color combination.

To the best of my knowledge this new variety is the result of a cross between the varieties Camelia and Pink Pearl. Hand cross-pollination was done by me but no precaution was taken to prevent admixture of other varieties by bees or insects.

The new variety has been asexually reproduced through several generations and its characteristics have proved to be permanently fixed.

The illustration making a part of this application shows two views of the flowers of this new variety, in as nearly their true colors as it was possible for the artist to depict them. Both figures are reduced in size although Fig. 1 is of course greatly reduced. Fig. 1 indicates the shape and symmetry of the entire spike and the number of buds and blossoms with their sequence of opening. Fig. 2 is a detailed true-color picture of some of the buds, open flowers and spent flowers.

In the folowing detailed description, color references indicate Ridgway's Color Standards and Nomenclature, 1912 edition.

*The plant*

Growth: Very vigorous, averaging 58 inches in height and sometimes attaining a height of 5½ feet. Propagates readily. Hardy, superior to most varieties in the winter season.

Blooming: Each spike opens 5 to 7 of its large flowers at one time. Successive blooms open, totalling an average of 20 florets to each spike. The variety is an early bloomer—planted late in January, it will bloom the latter part of April in this climate.

Stems: Straight; stiff; Parrot Green (Pl. vi); diameter at base is as much as ¾ to 1 inch.

Foliage: Spinach Green (Pl. v); average 2 inches wide and 34 inches high.

Disease resistance: Very resistant to diseases to which gladiolus varieties are usually subject.

Corms: Unusually healthy; smooth and high crowned. Average 3 inches in diameter from adult plants.

*The flower*

Spike: Long; slender; has 18 to 22 buds and flowers, 3 or 4 opening the first day, following which 5 to 7 are open at one time until all have opened.

Bud:

*Size.*—Opening buds are 3½ to 4 inches long.

*Opening.*—Eight buds show color at one time, 3 to 4 open first day.

*Color.*—Geranium Pink to Begonia Rose (Pl. i).

Flower:

*Arrangement.*—Flowers are closely and evenly spaced on the spike and all face in the same direction.

*Size.*—Lower blooms average 6 inches across when permitted to bloom on the plant in the field. Upper blooms are progressively smaller. When cut in the bud stage and opened artificially, the blooms are not so large.

*Form.*—Wide open; regular; six petals, three upper ones larger than others.

*Keeping qualities.*—Keep and ship exceptionally well.

Petals:

*Shape.*—Upper petals are unusually wide; almost round, unwrinkled and unnotched.

*Size.*—Three upper petals are 2 to 3 inches wide; lower petals 1½ to 2 inches wide.

*Aspect.*—Substance heavy; surface smooth.

*Fragrance.*—None.

*Color.*—Exceedingly smooth and soft. The exact shade is not shown in Ridgway's although the nearest is in Plate i and lies between La France Pink and Begonia Rose. From the edge toward the center the color diminishes from Begonia Rose to La France Pink which blends into the throat or lower portion of the petal which is largely cream color shaded with a touch of Martius Yellow (Pl. iv), the latter being more evident on flowers opened in the field. A streak of white extending through the pink the entire length of the petal is a characteristic of the variety.

Reproductive organs:

*Stamens.*—Large; white, with open side of anthers edge with Amparo Purple (Pl. xi).

*Pistils.*—Three-pronged, extending considerably beyond stamens; white.

*Comparisons*

My new variety resembles the varieties Phaenomen and Mr. W. H. Phipps more than any other known varieties, but differs from them principally as follows:

1. My variety is taller than Phaenomen.
2. My variety has longer spike than Phaenomen.

3. My variety has larger flowers than Phaenomen.

4. Flowers of my variety have Cream to Martius Yellow throat, while neither Phaenomen nor Mr. W. H. Phipps has a throat of this color.

5. The spike of my new variety is very slender at the tip, while that of Mr. W. H. Phipps is very stubby.

6. My variety is more disease resistant than Mr. W. H. Phipps.

7. My variety is a much better propagator than Mr. W. H. Phipps.

Having thus disclosed my invention, I claim:

The new and distinct variety of gladiolus plant with novel combination of features substantially as shown and described, characterized particularly by its hardiness and vigorous growth; its long and slender spike; the regular and compact arrangement of flowers on its spikes; and the many very large flowers having rounded slightly wrinkled petals, excellent keeping qualities, and distinctive soft clear coloring as indicated.

ELIZABETH A. BRIGGS.